(12) United States Patent
Horsels et al.

(10) Patent No.: US 8,618,334 B2
(45) Date of Patent: *Dec. 31, 2013

(54) CYCLOHEXANONE PRODUCTION PROCESS WITH MODIFIED POST-DISTILLATION

(75) Inventors: Marleen Horsels, Munstergeleen (NL); Rudy Francols Marla Jozef Parton, Winkelse (BE); Johan Thomas Tinge, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 438 days.

This patent is subject to a terminal disclaimer.

(21) Appl. No.: 12/809,257

(22) PCT Filed: Dec. 16, 2008

(86) PCT No.: PCT/EP2008/067635
§ 371 (c)(1),
(2), (4) Date: Oct. 25, 2010

(87) PCT Pub. No.: WO2009/080621
PCT Pub. Date: Jul. 2, 2009

(65) Prior Publication Data
US 2011/0054142 A1  Mar. 3, 2011

(30) Foreign Application Priority Data
Dec. 20, 2007  (EP) .................................. 07024764

(51) Int. Cl.
*C08G 8/10* (2006.01)
*B01D 3/10* (2006.01)
*B01D 3/32* (2006.01)
*B01J 19/32* (2006.01)

(52) U.S. Cl.
USPC ........... 568/366; 202/154; 202/155; 202/173; 202/176; 202/205; 203/78; 203/80; 203/99; 203/DIG. 16; 203/DIG. 19; 422/129; 422/187; 261/114.5; 568/362

(58) Field of Classification Search
USPC ............ 202/154, 155, 173, 176, 205; 203/78, 203/80, 99, DIG. 19, DIG. 16; 568/362, 366; 422/129, 187; 261/114.5
See application file for complete search history.

(56) References Cited

U.S. PATENT DOCUMENTS 2,829,166 A  4/1958  Joris et al.
3,305,586 A  2/1967  Bernard
(Continued)

FOREIGN PATENT DOCUMENTS

EP  0 557 821  9/1993

OTHER PUBLICATIONS

International Search Report for PCT/EP2008/067635, mailed Apr. 23, 2009.
Written Opinion of the International Searching Authority for PCT/EP2008/067635, mailed Apr. 23, 2009.

*Primary Examiner* — Virginia Manoharan
(74) *Attorney, Agent, or Firm* — Nixon & Vanderhye P.C.

(57) ABSTRACT

Methods for continuously preparing cyclohexanone from phenol make use of a catalyst having at least one catalytically active metal selected from platinum and palladium. The process includes enriching phenol in a distillation fraction as compared to a subsequent fraction, wherein the subsequent fraction includes phenol and side-products having a higher boiling point than phenol. Distillation is carried out in a vacuum distillation column equipped with trays in the lower part of the column. In an upper part of the column, i.e., in the part above the feed inlet, packing material is present instead of trays in at least part thereof. The packing material has a comparable or improved separating efficiency, and provides a reduction of the pressure drop by at least 30%, preferably more than 50%, as compared to the case with trays in the upper part, under otherwise similar distillation conditions.

16 Claims, 3 Drawing Sheets

(56) References Cited

U.S. PATENT DOCUMENTS

Figure 1:
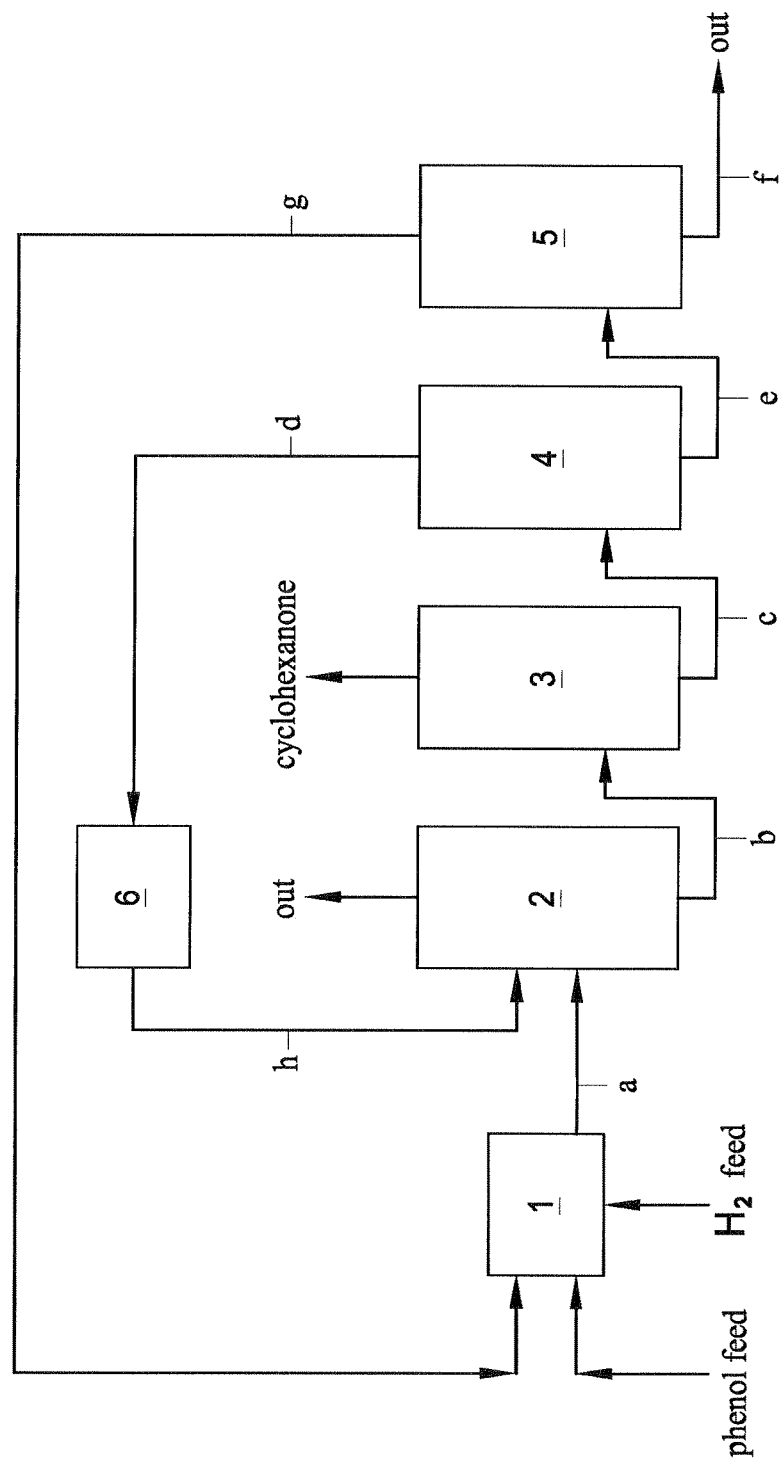

| | | | |
|---|---|---|---|
| 4,272,326 A | 6/1981 | Hertzog et al. | |
| 4,306,944 A * | 12/1981 | Murthy et al. | 203/77 |
| 4,457,807 A * | 7/1984 | Rulkens et al. | 203/72 |
| 5,131,984 A * | 7/1992 | Chan et al. | 203/6 |
| 6,855,248 B1 * | 2/2005 | Olivier et al. | 208/366 |
| 2006/0124441 A1 | 6/2006 | Benneker et al. | |
| 2009/0270656 A1 * | 10/2009 | Fukuoka et al. | 568/852 |

* cited by examiner

CYCLOHEXANONE PRODUCTION PROCESS WITH MODIFIED POST-DISTILLATION

This application is the U.S. national phase of international Application No. PCT/EP2008/067635, filed 16 Dec. 2008, which designated the U.S. and claims priority to European Application No. 07024764.8, filed 20 Dec. 2007, the entire contents of each of which are hereby incorporated by reference.

The invention relates to a method for the preparation of cyclohexanone from phenol and to a plant suitable for carrying out a method according to the invention.

Cyclohexanone can be employed as an industrial solvent or as an activator in oxidation reactions. It can also be used as an intermediate, inter alia in the production of adipic acid, cyclohexanone resins, caprolactam, nylon 6 or nylon 6,6.

Cyclohexanone is conventionally prepared from phenol by catalytic hydrogenation in a phenol hydrogenation reactor, e.g., using a platinum or a palladium catalyst. The reaction can be carried out in the liquid phase or the vapour phase. [Kirk-Othmer Encyclopedia of Chemical Technology, e.g. 3.sup.rd Edition, Vol 7 (1979) p. 410-416; I. Dodgson et al. "A low Cost Phenol to Cyclohexanone Process", Chemistry & Industry, 18, Dec. 1989, p 830-833; or M.T. Musser "Cyclohexanol and Cyclohexanone", Ullmann's Encyclopedia of Industrial Chemistry ($7^{th}$ Edition, 2007), (hereafter "Musser").

In the preparation of cyclohexanone from phenol, typically cyclohexanol (which can be considered an intermediate product useful for further conversion to cyclohexanone) and various undesirable side-products are formed. The cyclohexanone is typically recovered by a distillation process as a product rich in cyclohexanone (usually ≥90 wt. %) or as an essentially pure product ≥99 wt. %). In distillation, a fluid is separated into at least two fractions. When comparing two fractions, one may be called a "light" fraction, the other a "heavy" fraction. In particular when reference is made herein to a "light" fraction or a "heavy" fraction in relation to a separation by distillation, these terms are used herein relative to each other in a specific distillation step, to distinguished the fraction with the lower boiling point (the light fraction) from the fraction with the higher boiling point (the heavy fraction). Thus, a specific compound can be a "heavy" compound (mainly found in the heavy fraction) in a first distillation step, and a "light" compound (mainly found in the light fraction) in a second distillation step. As generally known, separation of a mixture into a heavy fraction and a light fraction is never absolute.

A conventional process for the preparation and recovery of cyclohexanone from phenol feedstock is schematically shown in FIG. 1.

Cyclohexanone is prepared in hydrogenation reaction section (1). This reaction section in particular comprises a hydrogenation reactor (which during use is supplied with hydrogen and phenol) and may comprise additional equipment. See for instance FIG. 1 in Musser, or in U.S. Pat. No. 3,305,586. The hydrogenation may either take place in a vapour phase process or in a liquid phase process.

Cyclohexanone, (unreacted) phenol and side-products, such as cyclohexanol is usually recovered from the stream leaving the reaction section using a number of distillation sections, which conventionally are all equipped with trays. A distillation section, as used herein is an installation comprising one distillation column or a plurality of distillation columns in parallel, each having the same functionality, some of which may be vacuum distillation columns. Further this section may comprise other typical parts of distillation units.

In an optional first distillation section (2) (the pre-distillation section, i.e. a first part of a distillation section upstream of a distillation section wherein cyclohexanone is recovered) light components, e.g. benzene, cyclohexane, water are removed from the reaction product, which reaction product enters the distillation section (2) via conduit a and h, whereas cyclohexanone, residual phenol, cyclohexanol and other side-products leave the pre-distillation section as a bottom fraction via conduit b.

This bottom fraction is distilled in a second distillation section (3) (the main distillation section, i.e. wherein cyclohexanone is recovered). Herein cyclohexanone is recovered from the process stream as a light fraction. The heavy fraction of distillation section (3) contains residual phenol, cyclohexanol, various side-products, and in general still some cyclohexanone. This heavy fraction leaves the distillation section (3) via conduit c. Suitable distillation conditions are known in the art, see e.g. U.S. Pat. No. 2,829,166 or U.S. Pat. No. 3,076,810. From this heavy fraction, typically the valuable components residual phenol, cyclohexanol and cyclohexanone are recovered.

Cyclohexanol is typically recovered from this heavy fraction leaving the main distillation as a light fraction in a (first) post-distillation section (4) (post-distillation meaning downstream of the main distillation wherein cyclohexanone is recovered). This light fraction, which also contains some cyclohexanone, is a cyclohexanol-rich stream, usually comprising at least 70 wt. % cyclohexanol, in particular at least 80 wt. % cyclohexanol. This light fraction is subsequently led to a cyclohexanol dehydrogenation section (6) via conduit d (see e.g. Musser, paragraph 3.5). In cyclohexanol dehydrogenation section (6) cyclohexanol is partially dehydrogenated to form cyclohexanone. Typically, section (6) comprises a dehydrogenation reactor, and usually further an evaporator for evaporating the feed upstream of the reactor, and a condenser for condensing the product stream leaving the reaction. The cyclohexanone-enriched stream leaving section (6) is then led to pre-distillation section (2), via conduit h.

Phenol forms part of the bottom fraction of the first post-distillation. This bottom fraction is fed to a further post-distillation section (5), via conduit e, wherein remaining valuable components, mainly phenol and in general some cyclohexanone and some cyclohexanol, are recovered as the light fraction and returned to the phenol hydrogenation reaction section, via conduit g. The bottom fraction from the last post-distillation is typically discarded via conduit f, e.g. incinerated or used for steam generation in a boiler house. Alternatively, the bottom fraction may be used as a low-cost material for a residual product, e.g. tar, asphalt, shoe polish or the like.

The inventors have realised that in the above described process, severe fouling with heavy residues occurs in post-distillation section (5). The energy consumption in post-distillation section (5) (for a given cyclohexanone production capacity) of the plant increases in time and the separation efficiency in post-distillation section (5) decreases in time. Therefore the plant has to be shut down frequently (four times a year, each time for two to four days) to clean post-distillation section (5). This results in a considerable loss of production.

It is an object of the invention to provide a method for preparing cyclohexanone, wherein one or more of the above drawbacks are overcome or at least alleviated.

The inventors have found that it is possible to increase production capacity, reduce energy consumption and/or reduce fouling in a process for converting phenol to cyclohexanone by hydrogenation by modifying post-distillation section (5) by means of replacement of the trays in the upper part of this section by packing material having a comparable or improved separating efficiency, and a reduction of the pressure drop by at least 30%, preferably more than 50%, as compared with the replaced trays, and—except for bottom temperature and temperature and pressure profile over the column—under otherwise similar distillation conditions.

As meant herein the term "similar distillation conditions" means that, in a given column of specific dimensions, the top pressure and top temperature, as well as reflux are nearly identical, whereas bottom temperature and pressure, and temperature and pressure profile over the column will vary according to the height of the feed inlet and configuration of the column achieved by number of trays and type of packing.

As meant herein the term "upper part" means that at most in the whole part above the location where the feed enters into the column, packing material is present instead of the trays. The packing material may be random or structured packing, independent of its material construction (e.g. metal, ceramics, glass, etc.). The term "distillation conditions" means, as known to the skilled person, the total of e.g. feed rate, feed pressure, feed temperature, head pressure, top temperature, and reflux ratio. The term "lower part" as used in this application means the whole part at or below the location where the feed enters into the column.

Accordingly, the present invention relates to a method for continuously preparing cyclohexanone from phenol making use of a catalyst comprising at least one catalytically active metal selected from platinum and palladium comprising the steps of a) hydrogenating phenol to form a product stream comprising cyclohexanone and unreacted phenol;
b) separating at least part of the product stream, or at least part of the product stream from which one or more components having a lower boiling point than cyclohexanone have been removed, into a first fraction comprising cyclohexanone and a second fraction comprising phenol and cyclohexanol, using distillation;
c) separating the second fraction into a third fraction, rich in cyclohexanol, and a fourth fraction, rich in phenol, using distillation;
d) subjecting at least part of the fourth fraction to a further distillation step, thereby forming a fifth fraction and a sixth fraction, wherein the fifth fraction is enriched in phenol compared to the sixth fraction, and wherein the sixth fraction comprises side-products having a higher boiling point than phenol, and phenol, wherein step d) is carried out in a vacuum distillation column equipped with trays in the lower part of the column, and wherein in the upper part of the column, i.e. in the part above the feed inlet, packing material is present instead of trays in at least part of said upper part, which packing material has a comparable or improved separating efficiency, and provides a reduction of the pressure drop by at least 30%, preferably more than 50%, as compared to the case with trays in the upper part, under otherwise similar distillation conditions.

Where in this application the term "trays in at least part of said upper part" is used, this means that at least 30%, more preferably at least 50% and most preferably at least 80% of these trays are referred to (as to replacement by packing in the part above the feed inlet).

In an embodiment according to the invention, at least part of the sixth fraction is continuously or intermittently led to yet a further distillation step e), thereby forming a seventh fraction and an eight fraction, wherein the seventh fraction is enriched in phenol compared to the eight fraction, and wherein the eight fraction comprises side-products having a higher boiling point than phenol.

Preferably, also step e) is carried out in a vacuum distillation column equipped with trays in the lower part of the column, and wherein in the upper part of the column packing material is present instead of trays in at least part of said upper part, which packing material has a comparable or improved separating efficiency, and provides a reduction of the pressure drop by at least 30%, preferably more than 50%, as compared to the case with trays in the upper part, under otherwise similar distillation conditions.

In an embodiment of the invention, at least part of the fifth fraction comprising phenol is continuously or intermittently recycled to step a).

The invention further relates to a chemical plant suitable for carrying out a method according to the invention, the plant (see FIGS. 1, 2, and 3) comprising a phenol hydrogenation reaction section (1);
downstream of the phenol hydrogenation reaction section (1) a plurality of distillation sections, optionally including a pre-distillation section (2), for removing one or more light components from the product stream from the hydrogenation section and comprising sections (3), (4), (5), and optionally (7) respectively for separating the product stream of the phenol hydrogenation reaction section (1) into a first fraction (to be led out of the section (3) via conduit "cyclohexanone") and a second fraction (to be led to section (4) via conduit c), for separating said second fraction into a third fraction (to be led out of section (4) via conduit d) and a fourth fraction (to be led to section (5) via conduit e), for separating said fourth fraction into a fifth fraction (to be led out of section (5) via conduit g) and a sixth fraction (to be led to section (7) via conduit f), and optionally for separating said sixth fraction into a seventh fraction (to be led out of section (7) via i (FIGS. 2 and 3) and an eight fraction (to be led out of section (7) via conduit j, usually an outlet out of the plant), wherein the vacuum distillation columns of section (5) and optionally of section (7) are equipped with trays in the lower part of the column, i.e. in the part at or below the feed inlet, and wherein in the upper part of the column, i.e. in the part above the feed inlet, packing material is present instead of trays in at least part of said upper part, which packing material has a comparable or improved separating efficiency, and provides a reduction of the pressure drop by at least 30%, preferably more than 50%, as compared to the case with trays in the upper part, under otherwise similar distillation conditions.

Usually, the plant comprises a loop (comprising conduit d, dehydrogenation section (6), and conduit h) for converting at least part of the cyclohexanol in said third fraction from distillation section (4) into cyclohexanone and feeding the resulting stream into distillation section (2). Moreover, the plant usually comprises a recycling loop (comprising conduit g) for recycling at least part of said fifth fraction into hydrogenation reaction section (1).

FIG. 1 schematically shows a conventional installation for preparing cyclohexanone from phenol feedstock, which also represents an installation according to the invention if in the upper part of the column of section (5) packing material is present instead of trays in at least part of said upper part.

Figure 2:
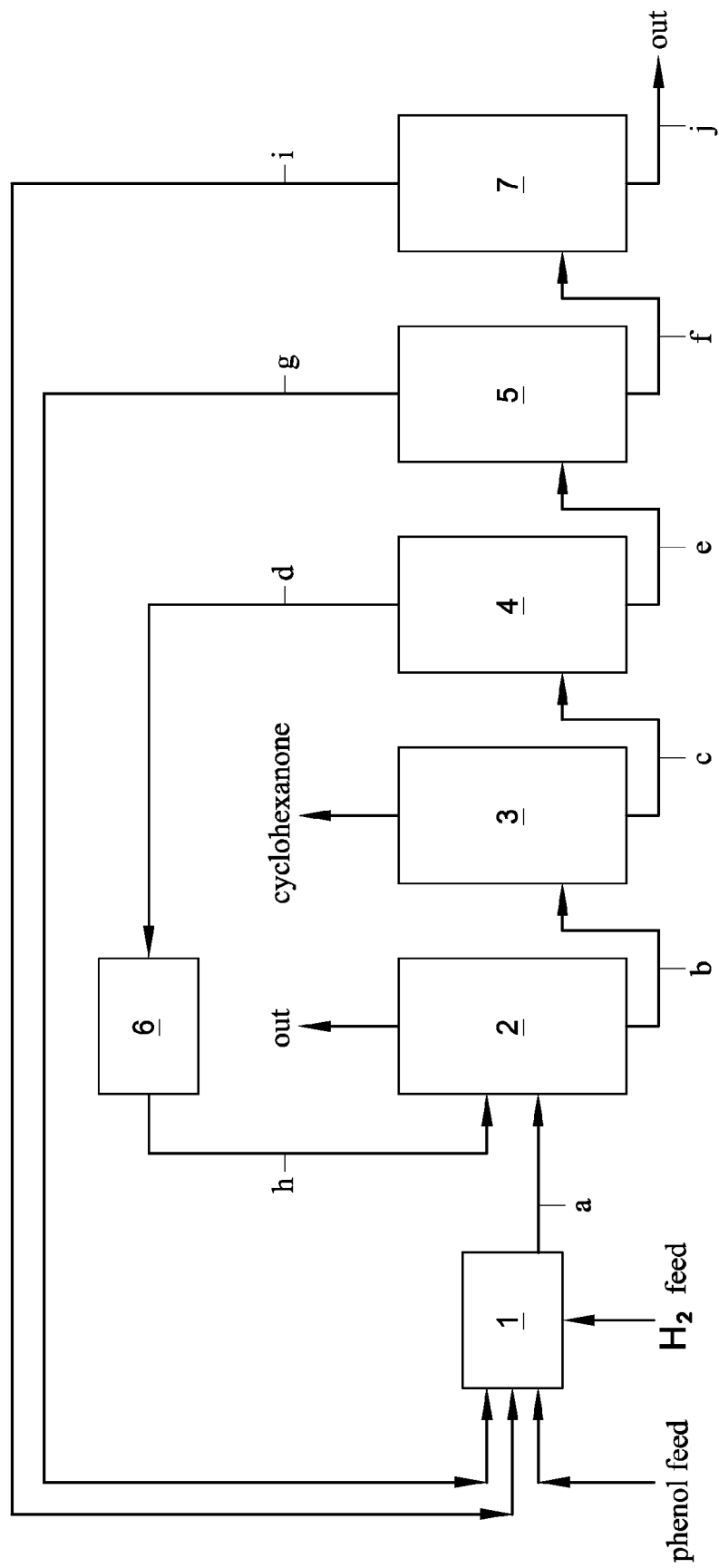

FIG. 2 schematically shows a plant according to the invention, wherein a recycling loop is present for recycling the fifth and/or seventh fraction to hydrogenation reaction section (1), wherein in the upper part of the columns of section (5) and optionally (7) packing material is present instead of trays in at least part of said upper part.

Figure 3:
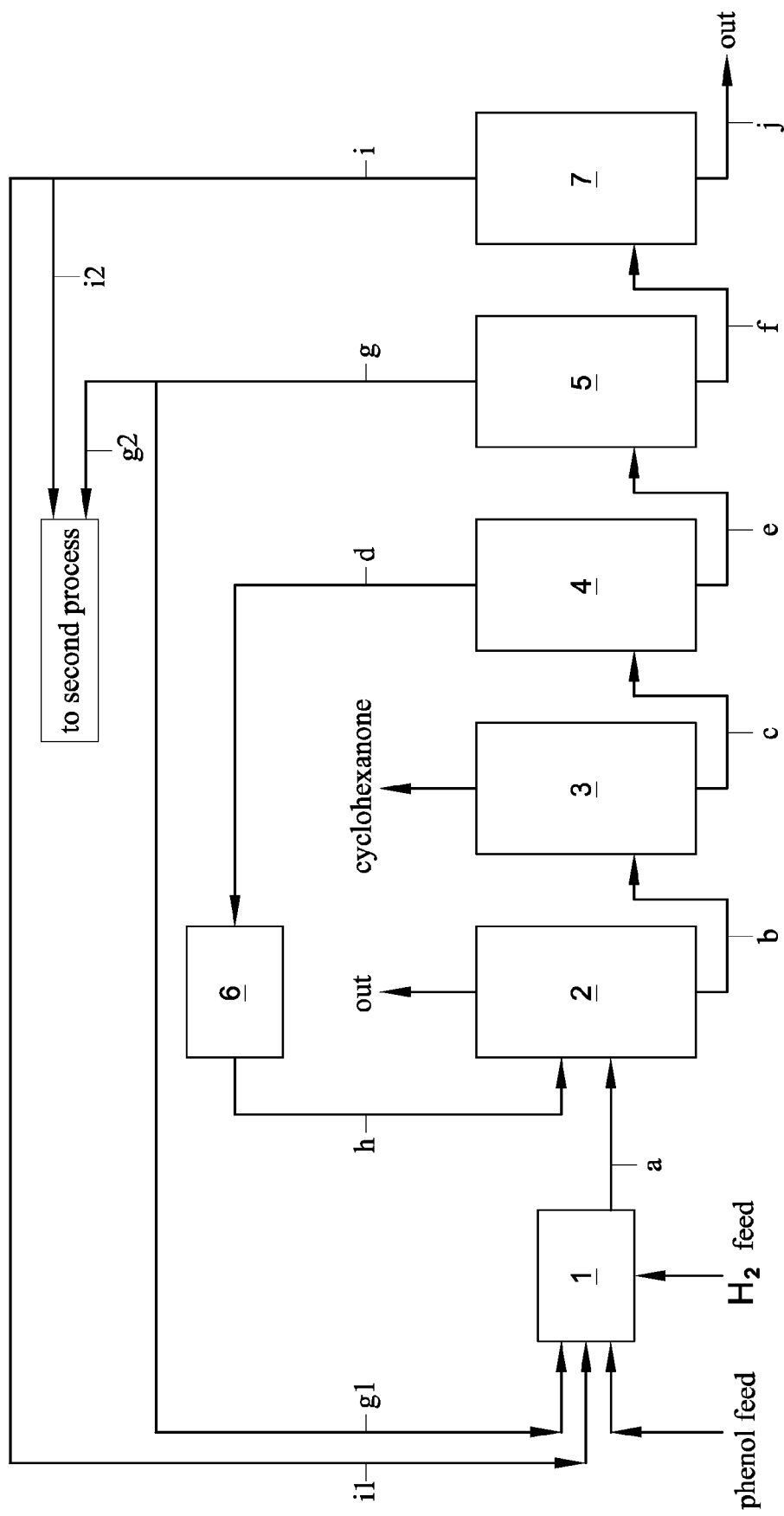

FIG. 3 schematically shows a plant according to the invention, wherein in the upper part of the columns of section (5) and optionally (7) packing material is present instead of trays in at least part of said upper part, wherein a conduit is present for leading the fifth and/or seventh fraction or part of any of these fractions into hydrogenation reaction section (1) and/or into an installation for carrying out another process.

As will be understood by the skilled person, the embodiments illustrated as examples in FIGS. 1, 2 and 3, discussed herein below in more detail, or parts thereof may be combined to provide alternative embodiments of the invention. It is to be noted that in these Figures feed streams to numbered sections are represented as separate streams, but it will be evident to the skilled person that streams fed into a section may be combined before entering the section, or may enter the section separately. E.g. streams fed into a section may be introduced into a vacuum distillation column of the section at different levels of the column.

According to the invention, production capacity is increased (because of less down time, and less fouling) and energy losses (due to fouling) are decreased. The inventors in particular have found that in a vacuum distillation column equipped with trays in the lower part of the column, and with packing in at least part of the upper part of the column, i.e. in the part above the feed inlet, which packing material has a comparable or improved separating efficiency, a reduction of the pressure drop by at least 30%, preferably more than 50% is achieved. Moreover, in such case, the bottom temperature is decreased substantially and surprisingly also significant less fouling occurs. In particular, the inventors found that a plant, e.g. as schematically shown in FIGS. 1, 2 and 3, wherein a method of the invention is carried out does not need to be shut down anymore so frequently for cleaning a distillation section, in particular section (5) as shown in the Figures.

It is to be noted that replacement of trays by packing material is not obvious for the skilled person, since it is well known that columns filled with packing material are subject to heavy fouling in distillations where heavies are present and/or formed. In general, in situ cleaning of packing material is not an option.

As mentioned above, the method of the invention can be combined with an extra post-distillation step (distillation section (7)). This extra post-distillation step avoids that the plant has to be shut-down for cleaning apart from the planned shut-downs, e.g. every 4 years. Also separation efficiency may be increased. Due to the extra post-distillation step e), post-distillation step d) (cf. section (5) in the Figures) requires less energy input. Because, if section (7) is used, relatively more phenol will be present in the bottom of section (5), the temperature and residence time of the liquid in the bottom of post-distillation column (5) will significantly be reduced, and consequently the amount of heavy residues produced therein is significantly lower. Accordingly, fouling of section (5) is further reduced.

The present invention also provides a method to increase capacity of existing plants (revamping) and to decrease maintenance costs.

In a method according to the invention, the pressure drop in the vacuum distillation column of post-distillation section (5) is significant reduced depending on the location (height) where the feed enters into the distillation column. In the present application the pressure drop is reduced with at least 30%, preferably more than 50%. Therefore, the temperature in the bottom is reduced with over 10° C. and less fouling of the column occurs.

The pressure drop can be further decreased by putting packing on all trays of the column, however it turned out that the column very rapidly fouled.

If post-distillation section (5) is followed by a further post-distillation section (7), than the bottom fraction of post-distillation section (5) is fed, via conduit f, to post-distillation section (7). The stream through conduit f contains remaining valuable components, mainly phenol and in general some cyclohexanone and some cyclohexanol, which may be recovered as the light fraction and—if desired—returned to the phenol hydrogenation reaction section (1), via conduit i (FIGS. 2 and 3).

The bottom fraction of the last post-distillation section (5) or (7), if present, is typically discarded via conduit f respectively j (out), e.g. incinerated or used for steam generation in a boiler house. Alternatively, the bottom fraction may be used as a low-cost material for a residual product, e.g. tar, asphalt, shoe polish or the like.

According to the present invention, fouling of post-distillation section (5) can even be reduced to such extent that it does not need to be cleaned for a period of a year. In combination with post-distillation section (7), wherein step e) is carried out, no cleaning of post-distillation section (5) is needed until the next regular plant stop, often with a frequency of e.g. once per 4 or more years. Post-distillation section (7) may need to be cleaned from time to time, e.g. once per year or less, but during such cleaning of post-distillation section (7) the plant can be operated without post-distillation section (7), i.e. without step e). Thus the plant does not have to be shut down.

Moreover, the present invention allows, if combined with post-distillation section (7), a lower amount of useful products (cyclohexanone and/or cyclohexanol and/or phenol, the latter two being precursors for cyclohexanone), but mainly phenol, in the bottom fraction of post-distillation (7) than without the modification of post-distillation section (5) with this invention.

Thus, the present invention allows the continuous production of cyclohexanone for a prolonged time, compared to a conventional method as described above. The reduced fouling by the implementation of packing above the location where the feed enters into the vacuum distillation column in post-distillation section (5), and optionally (7), improves the energy and separation efficiency of the cyclohexanone process. Moreover, additional plant shut downs for cleaning are reduced resulting in significantly increased production capacity.

When referred herein to a stream, a product or other composition, "rich in" or "enriched in" a specific component, this generally means that this component is the major component, and in particular that the component is present in a concentration of more than 50 wt.%. However, this lower limit may be different for specific streams and components.

In general, the first fraction is rich in cyclohexanone, and enriched in cyclohexanone compared to the product stream. Preferably, the first fraction comprises at least 99 wt.% cyclohexanone, more preferably at least 99.8 wt. % cyclohexanone.

The third fraction, rich in cyclohexanol, may in particular be a light fraction of the distillation step wherein the third fraction is formed, whereas the fourth fraction may in particular be a heavy fraction. The third fraction preferably comprises at least 70 wt. %, more preferably at least 80 wt. % cyclohexanol. The fourth fraction preferably comprises at least 65 wt. % phenol.

The fifth fraction, having a higher phenol content than the fourth fraction, will in particular be a light fraction of the distillation step wherein the fourth fraction is distilled, whereas the sixth fraction will in particular be a heavy fraction. The sixth fraction has a lower phenol content than the fourth fraction. The phenol concentration in the sixth fraction is preferably at least 20 wt. % and more preferably at least 25 wt. % phenol. A relatively high phenol concentration in the sixth fraction is advantageous, because enhanced phenol concentration reduces the boiling point of the sixth fraction, and formation of polymeric side-products (which are highly contributing to the fouling) is reduced.

Step b), wherein presence of a pre-distillation is optional, may be referred to as the main distillation step (as cyclohexanone is recovered in this step). Step c), d) and optionally e) may also be referred to as a first, a second and optionally a third post-distillation step, respectively.

One or more of the fractions from the post-distillation steps that are enriched in phenol may fully or partially be recycled, in particular to the hydrogenation step a). It is also possible to lead such a fraction or a part thereof into a second process other than the process for preparing cyclohexanone from phenol.

The hydrogenation of phenol can in principle be carried out in any way, in a vapour phase or in a liquid phase, e.g. based on any technology described in or referred to in Kirk-Othmer Encyclopedia of Chemical Technology $3^{rd}$ Edition, Vol 7, 1979 p. 410-416; I. Dodgson et al. "A low Cost Phenol to Cyclohexanone Process", Chemistry & Industry, 18, Dec. 1989, p 830-833; GB 890,095; Hancil and Beranek Chem. Eng. Sci., 25, 1970, p. 1121-1126; or Sakai et al. Nippon Kagaku Kaishi, 5, 1972, 821-829; Musser (in Ullmans's, see above); U.S. Pat. No. 2,829,166 or U.S. Pat. No. 3,076,810. The hydrogenation reaction section may comprise an internal recycling stream for recycling part of the stream leaving a reactor wherein the hydrogenation takes place. Product stream leaving the hydrogenation reaction section generally comprises cyclohexanone, cyclohexanol, phenol and side-products.

The distillation steps (pre-distillation, main distillation, and post-distillations) can be accomplished in a manner known in the art, per se. Suitable distillation conditions can routinely be determined by the skilled person, based on common general knowledge and optionally some routine testing. In particular the skilled person may consult the prior art cited herein. For optional step e), respectively section (7), a conventional vacuum distillation column can be used, e.g. a vacuum distillation column as described in the art for the preceding post-distillation steps. It is also possible to use a more simple distillation apparatus, such as a film-evaporator, in particular a one-pass film evaporator. A film-evaporator shows sufficient separation efficiency for suitably carrying out step e) and is particularly advantageous in that it reduces investments and that its simple design allows faster cleaning.

As indicated above, the process of the invention comprises the synthesis of cyclohexanone and a number of distillation steps, inter alia to recover cyclohexanone.

In FIG. 3 conduit i is split into conduit i1 arranged to recycle at least part of the light fraction from post-distillation section (7) to hydrogenation reaction section (1) and conduit i2, arranged to lead the light fraction or part thereof into an installation for carrying out a second process. It is also possible to omit conduit i1. Optionally conduit g (for the light fraction from post-distillation section (5)) is split into conduits g1, for recycling said light fraction or a part thereof to hydrogenation reaction section (1), and g2, for leading said light fraction of a part thereof into a second process.

As the second process, in principle any process can be used wherein use can be made of such fraction. In particular suitable second processes include phenol-formaldehyde resin production processes. Accordingly, conduits i2 and i2' and/or conduit g2 may in particular lead to a phenol-formaldehyde resin installation.

Alternatively or in addition, conduits d and/or h may be arranged to fully or partially leading a light fraction from post-distillation section (4), a light fraction from post-distillation section (5), respectively a product stream from section (6) into another process. In particular, any such other process can be used wherein cyclohexanol is a suitable reagent for producing the substance of interest, wherein cyclohexanol is a suitable solvent or wherein cyclohexanol is the substance of interest. Such other process may in particular be selected from the group of cyclohexane oxidation processes, cyclohexanol dehydrogenation processes, and adipic acid production processes.

The invention will now be illustrated by the following comparative experiments and examples.

COMPARATIVE EXPERIMENTS AND EXAMPLES

The comparative experiments were carried out in a conventional plant (with section (5) containing a vacuum distillation column equipped only with trays) wherein cyclohexanone is produced by hydrogenation of phenol, as schematically depicted in FIG. 1. For convenience of comparison with the examples according to the invention, the actual plant data were scaled to an annual plant capacity of 100 000 metric tons of essentially pure cyclohexanone. For the examples according to the invention, results are presented which were obtained by simulating a 100 000 metric tons per year plant modified according to the invention, as described below. The main unit of post-distillation section (5) (in the comparative experiments and in the Examples) is a vacuum distillation column with a diameter of 0.9 m and a height of 15 m, containing 25 trays of which 15 trays are located above the feed inlet. The vapour leaving the top of this column is liquefied in a condenser. Part of the obtained liquid is fed to the top of this column as reflux, and the other part, flow g, is led to the phenol hydrogenation reaction section (1). The required energy for the distillation process in the column is introduced by means of indirect heating via steam. Flow f containing amongst others side-products, phenol, cyclohexanone and cyclohexanol leaves the process via the bottom of the distillation column of post-distillation section (5).

In Examples I and II (according to the invention), the vacuum column of post-distillation section (5) is equipped with packing (structured packing 350 Y, with a separation efficiency equal to that of the 15 trays replaced) in all of the upper part, i.e. in the part above the feed inlet.

Comparative Experiment A

The cyclohexanone plant, consisting of a phenol hydrogenation reaction section, a recovery/purification section and a cyclohexanol converter section, as described before and depicted in FIG. 1, directly after cleaning of the whole plant including the bottom section and the reboiler of the vacuum distillation column in section (5), theoretically can be operated (if the production level reached directly after cleaning could be maintained without shut downs) at an annual production capacity of 100 000 metric tons of essentially pure cyclohexanone.

The distillation conditions in post-distillation section (5) were:
head pressure: 80 mbar (8 kPa)
bottom pressure: 205 mbar (20.5 kPa)
reflux ratio: 1.3.

Under these conditions, the following performance of the vacuum distillation column in post-distillation section (5) is observed one week after start-up:

| Flow | e | f | g |
|---|---|---|---|
| Mass flow (in kg per hour): | 1162 | 69.9 | 1092 |
| Composition (in mass fractions): | | | |
| cyclohexanone | 0.033 | 0.002 | 0.034 |
| cyclohexanol | 0.169 | 0.001 | 0.180 |
| phenol | 0.740 | 0.030 | 0.786 |
| residue | 0.058 | 0.967 | <0.0005 |

Under these conditions the bottom temperature in the vacuum distillation column of post-distillation section (5) was as high as 170° C. However, due to fouling of the bottom section, of the sieves in the pumps and of the reboiler of the vacuum distillation column in post-distillation section (5), separation and energy efficiency are deteriorating over time.

In order to maintain adequate operation of the plant, the plant had to be shut down every month for a period of 2-4 days to remove the fouling of the vacuum distillation column in post-distillation section (5). As a consequence of the fouling and the shut downs for cleaning a loss in the actual annual production capacity of the cyclohexanone plant of over 10 800 metric tons/year can be calculated.

Comparative Experiment B

The cyclohexanone plant, consisting of a phenol hydrogenation reaction section, a recovery/purification section and a cyclohexanol converter section, as described before and depicted in FIG. 1, directly after cleaning of the whole plant including the bottom section and the reboiler of the vacuum distillation column in section (5), theoretically can be operated (if the production level reached directly after cleaning could be maintained without shut downs) at an annual production capacity of 100 000 metric tons of essentially pure cyclohexanone. The distillation conditions in post-distillation section (5) were:
head pressure: 180 mbar (18 kPa)
bottom pressure: 355 mbar (35.5 kPa)
reflux ratio: 1.3.

Under these conditions, the following performance of the vacuum distillation column in post-distillation section (5) is observed one week after start-up:

| Flow | e | f | g |
|---|---|---|---|
| Mass flow (in kg per hour): | 1162 | 84.2 | 1078 |
| Composition (in mass fractions): | | | |
| cyclohexanone | 0.033 | 0.027 | 0.033 |
| cyclohexanol | 0.169 | 0.006 | 0.182 |
| phenol | 0.740 | 0.161 | 0.785 |
| residue | 0.058 | 0.806 | <0.0005 |

Under these conditions the bottom temperature in the vacuum distillation column of post-distillation section (5) was as high as 164° C. However, due to fouling of the bottom section, of the sieves in the pumps and of the reboiler of the vacuum distillation column in post-distillation section (5) separation and energy efficiency are deteriorating over time.

In order to maintain adequate operation of the plant, the plant had to be shut down every 3 months for a period of 2-4 days to remove the fouling of the vacuum distillation column in post-distillation section (5). As a consequence of the fouling and the shut downs for cleaning a loss in the actual annual production capacity of the cyclohexanone plant of over 3 600 metric tons/year can be calculated.

Example I

The cyclohexanone plant, consisting of a phenol hydrogenation reaction section, a recovery/purification section and a cyclohexanol converter section, as described before and as depicted in FIG. 1, directly after start-up of the clean plant, theoretically can be operated at an annual production capacity of 100 000 metric tons of essentially pure cyclohexanone. In this example, the vacuum distillation column in distillation section (5) is equipped with structured packing in the upper part of the column, replacing 15 trays. Furthermore, the distillation conditions were kept similar to those in comparative example A.
head pressure: 80 mbar (8 kPa)
bottom pressure: 135 mbar (13.5 kPa)
reflux ratio: 1.3.

Under these conditions, the following performance of the vacuum distillation column in post-distillation section (5) is observed one week after start-up:

| Flow | e | f | g |
|---|---|---|---|
| Mass flow (in kg per hour): | 1162 | 69.7 | 1092 |
| Composition (in mass fractions): | | | |
| cyclohexanone | 0.033 | 0.001 | 0.035 |
| cyclohexanol | 0.169 | 0.001 | 0.180 |
| phenol | 0.740 | 0.030 | 0.785 |
| residue | 0.058 | 0.968 | <0.0005 |

Under these conditions the bottom temperature in the vacuum distillation column of post-distillation section (5) was as low as 156° C. Fouling was significantly reduced. In order to maintain adequate operation of the plant, the plant had to be shut down every 8 months for a period of 2-4 days to remove the fouling of the vacuum distillation column in post-distillation section (5). As a consequence of the reduced fouling and shut downs for cleaning a gain in the actual annual production capacity of the cyclohexanone plant of over 9 000 metric tons/year can be reached.

Example II

The cyclohexanone plant, consisting of a phenol hydrogenation reaction section, a recovery/purification section and a cyclohexanol converter section, as described before and as depicted in FIG. 1, directly after start-up of the clean plant, theoretically can be operated at an annual production capacity of 100 000 metric tons of essentially pure cyclohexanone. In this example the vacuum distillation column in distillation section (5) is equipped with structured packing in the upper part of the column, replacing 15 trays. Furthermore, the distillation conditions were kept similar to those in comparative example B.

head pressure: 180 mbar (18 kPa)
bottom pressure: 282 mbar (28.2 kPa)
reflux ratio: 1.3.

Under these conditions, the following performance of the vacuum distillation column in post-distillation section (5) is observed one week after start-up:

| Flow | e | f | g |
|---|---|---|---|
| Mass flow (in kg per hour): | 1162 | 83.9 | 1078 |
| Composition (in mass fractions): | | | |
| cyclohexanone | 0.033 | 0.024 | 0.033 |
| cyclohexanol | 0.169 | 0.007 | 0.182 |
| phenol | 0.740 | 0.161 | 0.785 |
| residue | 0.058 | 0.808 | <0.0005 |

Under these conditions the bottom temperature of the vacuum distillation column in post-distillation section (5) was as low as 155° C. Fouling was significantly reduced. In order to maintain adequate operation of the plant, the plant had to be shut down every 12 months for a period of 2-4 days to remove the fouling of the vacuum distillation column in post-distillation section (5). As a consequence of the reduced fouling and shut downs for cleaning a gain in the actual annual production capacity of the cyclohexanone plant of approximately 2 700 metric tons/year can be reached.

The invention claimed is:
1. A process for continuously preparing cyclohexanone from phenol comprising the steps of:
(a) hydrogenating phenol in the presence of a catalyst comprising at least one of platinum and palladium as a catalytically active metal to form a product stream comprising cyclohexanone and unreacted phenol;
(b) separating at least part of the product stream, or at least part of the product stream from which one or more components having a lower boiling point than cyclohexanone have been removed, into a first fraction comprising cyclohexanone and a second fraction comprising phenol and cyclohexanol, using distillation;
(c) separating the second fraction into a third fraction, rich in cyclohexanol, and a fourth fraction, rich in phenol and, using distillation; and
(d) subjecting at least part of the fourth fraction to a further distillation step, thereby forming a fifth fraction and a sixth fraction, wherein the fifth fraction is enriched in phenol compared to the sixth fraction, and wherein the sixth fraction comprises phenol and side-products having a higher boiling point than phenol, and wherein
step (d) is practiced by carrying out the further distillation step in a vacuum distillation column equipped with trays in a lower part of the further distillation column, and wherein
the further distillation column includes packing material instead of trays in at least part of an upper part of the further distillation column above a feed inlet thereof, and wherein
the packing material in at least part of the upper part of the further distillation column has at least a comparable separating efficiency, and provides a reduction of pressure drop by at least 30%, as compared to use of trays in the upper part thereof, under otherwise similar distillation conditions.

2. The process according to claim 1, wherein the process further comprises continuously or intermittently separating at least part of the sixth fraction to yet another further distillation step (e), thereby forming a seventh fraction and an eighth fraction, wherein the seventh fraction is enriched in phenol as compared to the eighth fraction, and wherein the eighth fraction comprises side-products having a higher boiling point than phenol.

3. The process according to claim 2, wherein
step (e) is practiced by carrying out the another further distillation in another vacuum distillation column equipped with trays in a lower part of the columne at or below a feed inlet to the another vacuum distillation column, and wherein
the another vacuum distillation column includes packing material instead of trays in at least part of an upper part of the another distillation column above a feed inlet thereof, and wherein
the packing material in at least part of the upper part of the another distillation column has at least a comparable separating efficiency, and provides a reduction of pressure drop by at least 30%, as compared to use of trays in the upper part thereof, under otherwise similar distillation conditions.

4. The process according to claim 1, wherein at least part of the fifth fraction comprising phenol is continuously or intermittently recycled to step (a).

5. The process according to claim 2, wherein at least part of the fifth fraction, at least part of the seventh fraction comprising phenol, or at least part of both the fifth and seventh fractions is continuously or intermittently recycled to step a).

6. The process according to claim 1, wherein at least part of the fifth fraction, at least part of the seventh fraction comprising phenol, or at least part of both the fifth and seventh fractions is continuously or intermittently introduced into a second process other than the process for preparing cyclohexanone from phenol.

7. The process according to claim 6, wherein the second process is a process for preparing a formaldehyde-phenol resin.

8. The process according to claim 1, wherein the at least part of the third fraction is continuously or intermittently introduced into a second process other than the process for preparing cyclohexanone from phenol.

9. The process according to claim 8, wherein the second process is a cyclohexane oxidation process, in which cyclohexanol and/or cyclohexanone is produced from cyclohexane.

10. The process according to claim 8, wherein the second process is a cyclohexanol dehydrogenation process, which comprises converting cyclohexanol at least partially converted into cyclohexanone in a cyclohexanol converter, and thereafter in the second process separating cyclohexanone from residual cyclohexanol and recycling side-product originating from the process for preparing cyclohexanone from phenol.

11. The process according to claim 8, wherein the second process is an adipic acid production process, wherein cyclohexanol is converted into adipic acid.

12. A chemical plant suitable for carrying out a method according to claim 1, comprising
a phenol hydrogenation reaction section for conducting step (a); and
a plurality of distillation sections downstream of the phenol hydrogenation reaction section, optionally including a pre-distillation section, for removing one or more light components from a product stream obtained from the hydrogenation section, wherein
the plurality of distillation sections comprises first, second and third distillation sections, and optionally a fourth distillation section, respectively for separating the product stream of the phenol hydrogenation reaction section into a first cyclohexanone fraction and a second fraction, for separating the second fraction into a third fraction and a fourth fraction, for separating the fourth fraction into a fifth fraction and a sixth fraction, and optionally for separating the sixth fraction into a seventh fraction and an eighth fraction wherien
the third distillation section, and optionally the fourth distillation section comprises a respective vacuum distillation column equipped with trays in a lower part of the column, and wherein at least a part of an upper part of the column, above a feed inlet thereof includes packing material instead of trays, wherein the packing material has at least a comparable separating efficiency, and provides a reduction of pressure drop by at least 30%, as compared to use of trays in the upper part thereof, under otherwise similar distillation conditions.

13. The chemical plant according to claim 12, further comprising a pre-distillation section and a loop for converting at least part of the cyclohexanol in the third fraction into cyclohexanone and feeding the resulting stream into the pre-distillation section.

14. The chemical plant according to claim 12, further comprising a conduit for leading at least one fraction or a part thereof selected from the group consisting of light fractions from at least one of the second, third, and optionally fourth, distillation sections to a different installation for preparing a useful substance.

15. The chemical plant according to claim 13, further comprising recycling loop for recycling at least part of the fifth fraction, and optionally a part of the seventh fraction, into hydrogenation reaction section.

16. The chemical plant according to claim 14, wherein the different installation an installation selected from the group consisting of installations for dehydrogenating cyclohexanol, installations for preparing adipic acid, installations for oxidizing cyclohexane and installations for preparing a formaldehyde-phenol resin.

* * * * *